US008834539B2

(12) United States Patent
Keren et al.

(10) Patent No.: US 8,834,539 B2
(45) Date of Patent: Sep. 16, 2014

(54) SUPERELASTIC WASHER (75) Inventors: Dvir Keren, Tel Aviv (IL); Hadar Better, Tel Aviv (IL)

(73) Assignee: Nitilick Ltd., Tel Aviv (IL)

( * ) Notice: Subject to any disclaimer, the term of this patent is extended or adjusted under 35 U.S.C. 154(b) by 403 days.

(21) Appl. No.: 13/127,710

(22) PCT Filed: Nov. 19, 2009

(86) PCT No.: PCT/IB2009/055161
§ 371 (c)(1),
(2), (4) Date: May 5, 2011

(87) PCT Pub. No.: WO2010/058358
PCT Pub. Date: May 27, 2010

(65) Prior Publication Data
US 2011/0213425 A1    Sep. 1, 2011

Related U.S. Application Data (60) Provisional application No. 61/116,660, filed on Nov. 21, 2008.

(51) Int. Cl.
*A61B 17/86*    (2006.01)
*F16B 43/00*    (2006.01)
*F16B 1/00*    (2006.01)
*A61B 17/80*    (2006.01)
*A61C 8/00*    (2006.01)
*A61B 17/00*    (2006.01)

(52) U.S. Cl.
CPC ............ *F16B 1/0014* (2013.01); *A61C 8/0068* (2013.01); *A61C 2201/007* (2013.01); *A61B 2017/00004* (2013.01); *A61B 17/8033* (2013.01); *F16B 43/00* (2013.01); *A61B 2017/00867* (2013.01); *A61B 17/8695* (2013.01)
USPC .......................... 606/305; 411/371.2; 411/531

(58) Field of Classification Search
USPC ......... 606/300–331; 411/82.5, 188, 399, 531, 411/161, 371.2
See application file for complete search history.

(56) References Cited

U.S. PATENT DOCUMENTS

| 3,801,954 A | 4/1974 | Dorrell |
| 4,294,559 A | 10/1981 | Schutzler |
| 4,450,616 A | 5/1984 | Morita |

(Continued)

FOREIGN PATENT DOCUMENTS

| WO | 9524166 A1 | 9/1995 |
| WO | 2006011127 A2 | 2/2006 |

OTHER PUBLICATIONS

International Application PCT/IB2009/055161 Search report dated Jul. 20, 2010.

(Continued)

*Primary Examiner* — Christopher Beccia
(74) *Attorney, Agent, or Firm* — K Kligler I.P. Services LTD.

(57) ABSTRACT

Fastening apparatus includes a fastener (30, 64, 120), including a threaded shaft (34, 126) having a thread diameter and a fastening element (36, 68, 124) having a head diameter, greater than the thread diameter. An annular washer (38, 40, 66, 70, 90, 100, 110, 122), including a shape memory material, is configured to fit over and surround the shaft and has an outer diameter no greater than the head diameter.

17 Claims, 9 Drawing Sheets

(56) References Cited

U.S. PATENT DOCUMENTS

| | | | |
|---|---|---|---|
| 4,619,568 A | | 10/1986 | Carstensen |
| 4,880,343 A | | 11/1989 | Matsumoto |
| 4,897,006 A | | 1/1990 | Blin |
| 5,366,331 A | * | 11/1994 | Erbes .................. 411/433 |
| 5,578,034 A | | 11/1996 | Estes |
| 5,584,695 A | | 12/1996 | Lal Sachdeva et al. |
| 5,772,378 A | * | 6/1998 | Keto-Tokoi ............. 411/432 |
| 5,791,847 A | | 8/1998 | Keto-Tokoi |
| 5,931,838 A | | 8/1999 | Vito |
| 2002/0187020 A1 | * | 12/2002 | Julien .................... 411/544 |
| 2003/0235481 A1 | | 12/2003 | Dunfee et al. |
| 2006/0107751 A1 | | 5/2006 | Wilkerson et al. |
| 2007/0259315 A1 | * | 11/2007 | Last-Pollak ............. 433/201.1 |
| 2008/0153060 A1 | * | 6/2008 | De Moyer ............... 433/173 |

OTHER PUBLICATIONS

Yousef et al., "Analysis of Changes in Implant Screws Subject to Occlusal Loading: A Preliminary Analysis," Implant Dentistry, vol. 14, issue 4, pp. 378-385, Dec. 2005.

European Patent Application # 09827254 Search report dated Jun. 28, 2013.

* cited by examiner

SUPERELASTIC WASHER

CROSS-REFERENCE TO RELATED APPLICATION

This application claims the benefit of U.S. Provisional Patent Application 61/116,660, filed Nov. 21, 2008, which is incorporated herein by reference.

FIELD OF THE INVENTION

The present invention relates generally to devices and methods for fastening and fixation, and specifically to washers.

BACKGROUND OF THE INVENTION

A washer is an annular structure with an opening along its central axis, which fits over the shaft of a threaded fastener, such as a screw or threaded stud. A fastening element, such as the head of the screw or a nut, compresses the washer as it is fastened. The term "washer," as used in the present patent application and in the claims, refers to any type of annular structure that meets these limitations. Spring washers are designed to apply a pre-load against the fastening element as it is screwed down and thus to prevent subsequent loosening of the fastener. Common types of spring washers include Belleville washers and wave washers.

Washers may be made from shape memory materials, such as Nitinol. For example, U.S. Patent Application Publication 2002/0187020, whose disclose is incorporated herein by reference, describes lock washers that are cut from a sheet or plate of Nitinol. The lock washer remains in its martensitic state in all normal conditions of use. The martensitic Nitinol initially yields during torquing of the nut to allow the nut to indent itself slightly into the washer. The resulting cold working of the washer material causes a transformation into stress-induced martensite, which is strong and elastic to resist further deformation and also exerts a preload on the bolt shank. The nut, indented into the lock washer, resists turning under vibration.

U.S. Pat. No. 3,801,954, whose disclosure is incorporated herein by reference, describes an electrical connector comprising a plug and receptacle coupled together using a screw or bayonet-type coupling and a heat-activatable, generally ring-shaped locking memory member made of a memory alloy, such as 55-Nitinol. The locking memory member is provided with original and intermediate shapes chosen for coaction with predetermined opposed annular surfaces provided on the plug and receptacle so that the application of moderate amounts of heat causes the locking memory member to rigidly lock the plug and receptacle in coupled engagement.

U.S. Pat. No. 4,450,616, whose disclosure is incorporated herein by reference, describes a method of insuring the tightness of a fastener. A three-dimensional annular member is formed in an austenite phase using a press. It is cooled to a temperature lower than the temperature for starting an austenite transformation, and the fastener is fastened with the annular member to flatten the annular member. The temperature of the annular member is then returned to a higher-than-austenite temperature so that the recovery power of the annular member for returning the annular member to the three-dimensional shape in the austenite phase generates a fastening force for the fastener.

SUMMARY OF THE INVENTION

Embodiments of the present invention that are described hereinbelow provide improved devices and methods for fixation of threaded fasteners using shape memory materials.

There is therefore provided, in accordance with an embodiment of the present invention, fastening apparatus, including a fastener, which includes a threaded shaft having a thread diameter and a fastening element having a head diameter, greater than the thread diameter. An annular washer, including a shape memory material, is configured to fit over and surround the shaft and which has an outer diameter no greater than the head diameter.

In some embodiments, the shape memory material is formed so as to describe a circumferential wave in an austenitic state of the material. In other embodiments, the shape memory material is formed as a ring, and the annular washer includes an ancillary structure configured to engender a circumferential deformation of the ring as the fastener is closed. The annular washer may be fixedly connected to the fastener.

There is also provided, in accordance with an embodiment of the present invention, a fastening device, including a central ring made from a shape memory material and having a central axis. An annular ancillary structure is coupled to the ring and configured to engender a circumferential deformation of the central ring in response to an axial force exerted on the structure.

Typically, the ancillary structure engenders a circumferential tension in the ring in response to the axial force. Additionally or alternatively, the central ring and the ancillary structure have a central opening configured to fit over and surround a threaded shaft of a fastener, having a head that exerts the axial force as the fastener is tightened into a socket.

In some embodiments, the ancillary structure includes axial struts, which engage the central ring at different, respective circumferential locations on opposing sides of the ring. Typically, the struts have respective inner ends, which engage the central ring, and respective outer ends, opposite the respective inner ends, and the ancillary structure includes first and second supporting rings, each of which is connected to the outer ends of the struts on a respective one of the opposing sides of the ring. The struts connected to each of the supporting rings are configured to deform the central ring at the respective circumferential locations, in response to the axial force, so as to cause the central ring to contact the other of the supporting rings. Optionally, the central ring may be one of a plurality of central rings, which are disposed along the axis and are interconnected by the axial struts.

In other embodiments, the ancillary structure includes first and second supporting rings, which are disposed along the axis on opposing sides of the central ring and have respective first and second inner surfaces describing respective first and second circumferential waves, which engage and deform the central ring in response to the axial force. Typically, the first and second supporting rings have flat outer surfaces, opposite the respective inner surfaces, for receiving the axial force, and the first and second inner surfaces are configured so that the first and second circumferential waves interlock. Optionally, the central ring may be one of a plurality of central rings, which are disposed along the axis and are interconnected with multiple supporting rings with respective circumferential waves.

There is additionally provided, in accordance with an embodiment of the present invention, apparatus for fixation, including an implant, which is configured to be inserted into a bone and which includes a threaded receptacle having a thread diameter. A fixture is configured to protrude out of the bone and includes a socket for alignment with the threaded receptacle, the socket having a socket diameter greater than the thread diameter. A fastener includes a threaded shaft, which is configured to be screwed into the threaded receptacle, and a head, which is sized so as to fit closely inside the socket. An annular washer, including a shape memory material, is configured and sized to fit inside the socket while surrounding the shaft of the fastener so as to be compressed by the head as the fastener is screwed into the socket.

There is further provided, in accordance with an embodiment of the present invention, a method for closing a fastener that includes a threaded shaft having a thread diameter and a fastening element having a head diameter, greater than the thread diameter. The method includes fitting an annular washer, which includes a shape memory material and has an outer diameter no greater than the head diameter, over the threaded shaft of the fastener. The fastening element is turned so that the head compresses the washer as the fastener is closed.

In a disclosed embodiment, turning the fastening element includes cooling the washer to below an austenitic temperature or the shape memory material, and closing the fastener while the washer is cooled, wherein the washer is permitted to warm to above the austenitic temperature after the fastener has been closed.

There is moreover provided, in accordance with an embodiment of the present invention, a fastening device, including an annular structure, which includes an elastic element and which is configured to fit over a shaft of a threaded fastener and to create a tension in the elastic element in response to an axial force exerted on the device as the fastener is tightened. Typically, the elastic element includes a shape memory material, such as Nitinol.

The present invention will be more fully understood from the following detailed description of the embodiments thereof, taken together with the drawings in which:

DETAILED DESCRIPTION OF EMBODIMENTS

Figure 1:
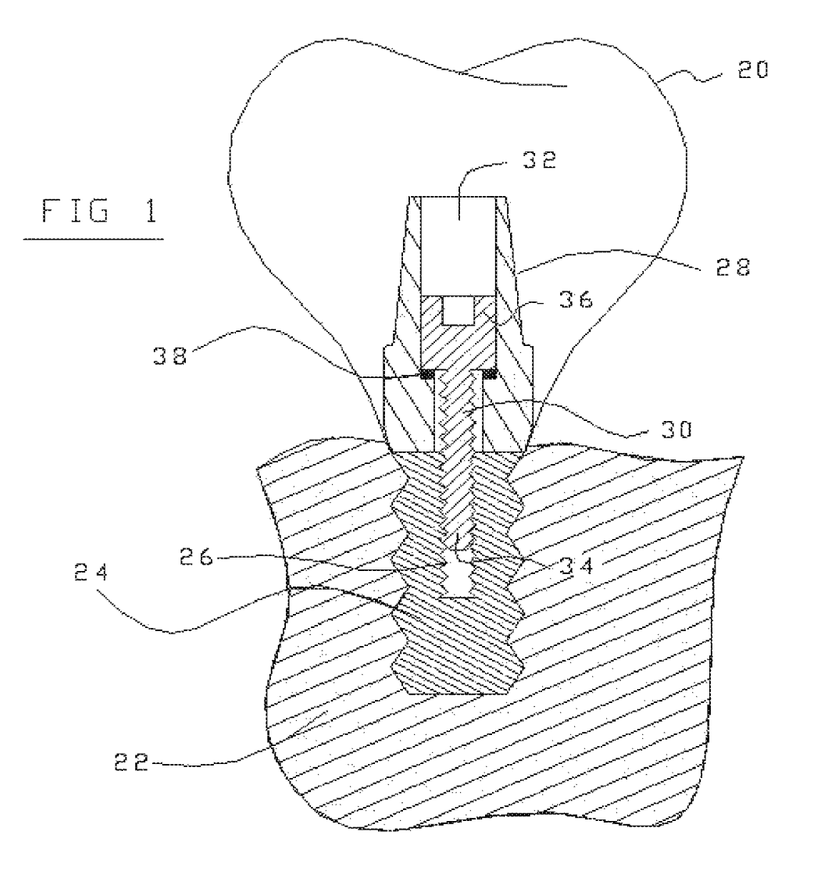
FIG. 1 is a schematic, sectional view of a dental prosthesis fixed to a bone, in accordance with an embodiment of the present invention.

FIG. 1 is a schematic, sectional view of a dental prosthesis 20 fixed to a bone 22, in accordance with an embodiment of the present invention. This embodiment is shown here by way of example, in order to illustrate features and advantages of certain novel types of fastening devices that are described hereinbelow. The principles of this embodiment may likewise be applied in other settings, however, including both medical and non-medical applications.

To install prosthesis 20, a dentist inserts an implant 24 into bone 22 (in this case the jaw bone). Implant 24 comprises a threaded receptacle 26. The dentist then screws an abutment 28 onto the implant using a threaded fastener 30 (in this case a screw). Abutment 28 protrudes out of the bone and provides a base for prosthesis 20. The prosthesis may then be glued on or screwed onto the abutment. In the case of a bridge or denture, multiple implants and screws may be used to hold the prosthesis in place. Alternatively, a ball attachment may be screwed to an implant, and a denture may then be fixed with friction to the ball.

Thus, although FIG. 1 shows a simple, single-tooth prosthesis, the principles of the present invention may be used in any of these applications to attach various types of fixtures to appropriate implants, as well as other types of applications described below. The term "fixture" should therefore be understood, in the context of the present patent application and in the claims, as referring to any sort of element that can be attached by a threaded fastener to an implant, including (but not limited to) abutments, crowns, bridges, dentures and other types of prosthetics.

Abutment 28 comprises a socket 32, which aligns with receptacle 26. The diameter of the socket is typically greater than the thread diameter, but the difference in diameters may be small—commonly less than 0.2 mm—due to size constraints.

Fastener 30 comprises a threaded shaft 34, which screws into threaded receptacle 26, and a head 36, which serves as a fastening element and is sized so as to fit closely inside socket 32. "Closely" in this sense means that the socket is only as large as is required to permit head 36 to be inserted and turned in the socket. Typically, in the type of embodiment that is shown in FIG. 1, the clearance between the head diameter and socket diameter is less than 0.2 mm and may be considerably less. As noted above, the size constraints of dental applications, coupled with the need for mechanical strength, militate strongly against making receptacles and sockets any larger than the minimum required to accommodate the fastening hardware.

In this situation, when conventional fastening hardware is used, the dentist must apply a large screwing force to fix fastener 30 securely in receptacle 26, and therefore runs the risk of stripping or breaking the fastener or receptacle. On the other hand, pressure on prosthesis 20 (as the patient chews, for example) will tend to relax the grip of the fastener over time, leading to loosening of the prosthesis. Conventional lock washers, if made small enough to fit into the space beneath head 36, cannot store sufficient elastic energy to overcome these problems.

Therefore, in the present embodiment, an annular washer 38, comprising a shape memory material (such as Nitinol), fits inside socket 32 below head 36, surrounding shaft 34 of fastener 30. The outer diameter of the washer is typically no greater than the diameter of the head, and may be smaller (although in some cases it may be slightly larger). Head 36 compresses the washer against the inner shoulder of socket 32 as the fastener is closed. Use of this washer permits the fastener to be closed safely and securely and to hold its position over time without loosening. Detailed designs of washers that may be used for this purpose are shown in the figures that follow. The principles of the present invention are not limited to these specific designs, however, and other types of shape memory washers (with diameters smaller than the head diameter) may likewise be used for the same purposes.

Shape memory alloys, such as Nitinol, are highly resilient in their austenitic state, above a certain transition temperature, but lose their resilience when cooled below this temperature to the martensitic state. Washer 38 is therefore produced so that at the normal operating temperature of fastener 30 (human body temperature in the embodiment of FIG. 1), the washer is in its austenitic state. Because of the exceptional resilience of the austenitic material, washer 38 exerts sufficient force against head 36 to hold the fastener in place, notwithstanding the small volume of the washer.

On the other hand, to facilitate secure attachment of abutment 28 to implant 24, washer 38 may be cooled to the martensitic state (using a commercially-available freezing spray, for example) before and/or during closure of fastener 30 in receptacle 26. As a result, only weak force is needed to compress the washer during the fastening action. Due to its shape memory, however, once the washer warms back up to the austenitic state (due simply to the patient's body heat in the present embodiment), it will exert a large force against head 36, as though it had never been cooled. Thus, the dentist is able to fasten the abutment in place using little force, without risk of stripping or breakage, while achieving the same outcome as if a strong fastening force had been applied.

Furthermore, because the shape memory property of materials such as Nitinol is stable over time, fastener 30 may be released easily, when necessary, by cooling washer 38.

Although the embodiment shown in FIG. 1 involves very small fastening components and weak forces, the types of shape memory washers and techniques that are described herein can also be useful in heavy-duty screw applications. Such washers and techniques enable fixation to be performed more easily than with conventional washers (without applying large forces), and/or to achieve stronger attachment while using the same amount of fixation force as in conventional techniques. Although the fastening element that is used in the pictured embodiment to close fastener 30 and compress washer 38 is the head of the threaded shaft, washers in accordance with embodiments of the present invention may similarly be used to secure other types of fastening elements, such as nuts.

The term "annular" is used, in the context of the present patent application and in the claims, in its conventional sense, to refer to objects having a ring shape. Although the washers shown in the figures that follow form closed rings, in some embodiments, not shown in the figures, it may be desirable that the circumference of the ring be broken. Such washers are also considered to be annular and within the scope of the present invention.

Figure 2A:
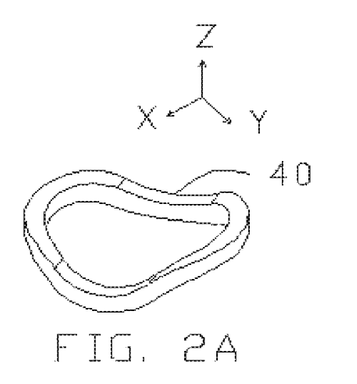
FIG. 2A is a schematic, pictorial view of a wave washer, in accordance with an embodiment of the present invention.
Figure 2B:
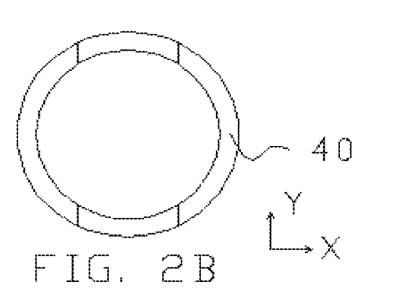
FIGS. 2B and 2C are schematic top and side views, respectively, of the wave washer of FIG. 2A.
Figure 2C:
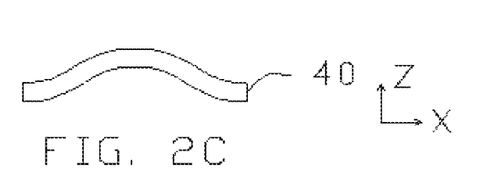

FIGS. 2A-2C schematically show a wave washer 40, in accordance with an embodiment of the present invention. FIG. 2A is a pictorial view, while FIGS. 2B and 2C are schematic top and side views, respectively. Washer 40, like the other washers shown in the figures that follow, may be used in place of washer 38 in the embodiment of FIG. 1.

Washer 40 comprises an annulus of shape memory material, such as Nitinol, which is formed so as to have a circumferential wave in the austenitic state of the material. The meaning of the term "circumferential wave" is illustrated in the figures: The axial (Z) coordinate of the annulus varies along the circumference of the washer as a function of angle about the axis. The circumferential wave in the pictured embodiments has a period of 180°, but other fractions of 360° (½, ⅓, ¼, etc.) may similarly be used.

Washer 40 can be made sufficiently thin—with the annulus itself no more than 0.2 mm thick—to fit below head 36 without protruding. The outer diameter of the washer is approximately 2 mm in this example, while the wave amplitude (Z-coordinate variation) is about 0.5 mm. When fastener 30 is fully screwed down into receptacle 26 (possibly after cooling the washer), the wave shape of the washer is flattened. Nevertheless, the washer continues to exert sufficient axial force against head 36 in order to prevent loosening of the fastener.

Figure 3:
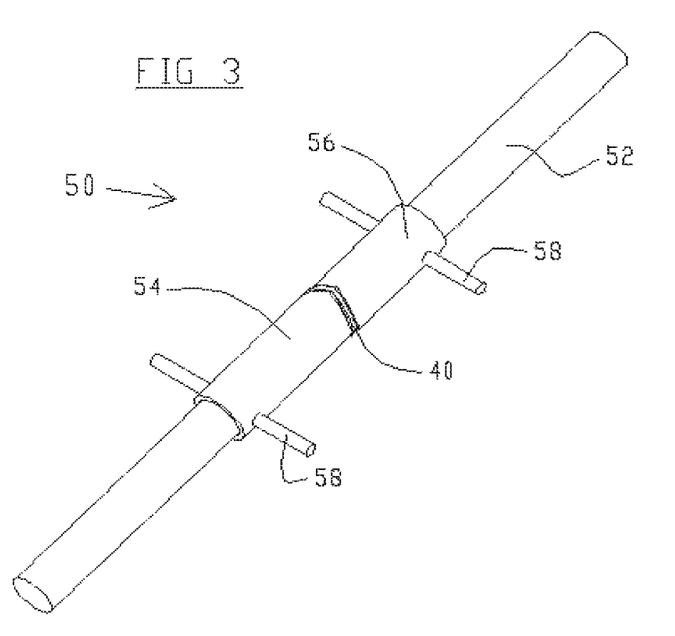
FIG. 3 is a schematic, pictorial view of a mold for producing wave washers, in accordance with an embodiment of the present invention.

FIG. 3 is a schematic, pictorial view of a mold 50 for producing washer 40, in accordance with an embodiment of the present invention. The washer is cut from a flat sheet of Nitinol and is assembled over a shaft 52. Tubular components 54 and 56 press the washer into the desired wave shape and are locked in place by pins 58. The mold with washer inside is inserted into an oven for heat treatment processing. The temperature and duration depend mainly on the heat transfer properties of the mold (in terms of both material and design). Typically the oven temperature is set to 500-650° C. for 3-20 minutes, whereby the Nitinol is reshaped at a temperature of 400-500° C. Alternatively, the washer may be cut from a tube of Nitinol using laser cutting or wire cutting, as are known in the art, and thus avoid the need for heat treatment.

Figure 4:
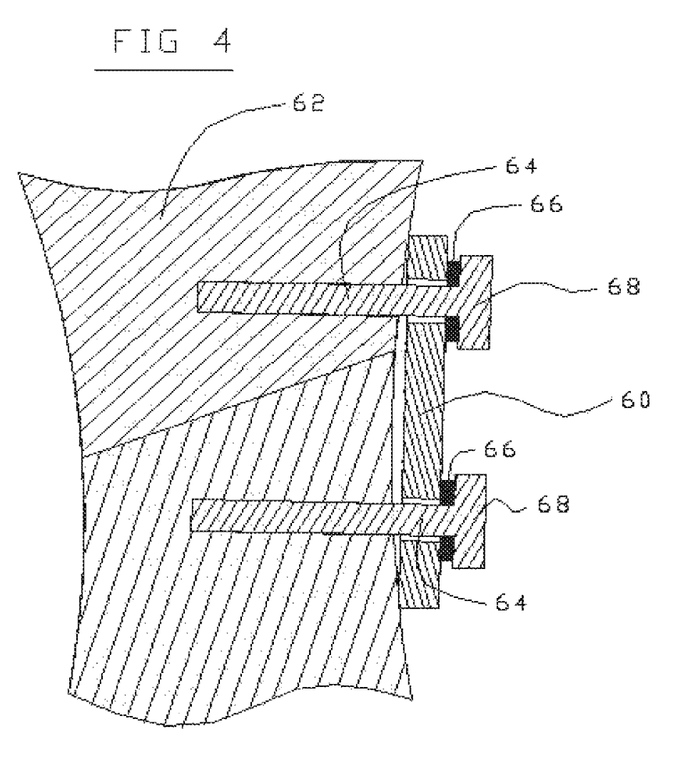
FIG. 4 is a schematic, sectional view showing fixation of a plate to a bone, in accordance with an embodiment of the present invention.

FIG. 4 is a schematic, sectional view showing fixation of a plate 60 to a bone 62, in accordance with another embodiment of the present invention in which shape memory washers are advantageous. Plates of this sort are used, for example, in orthopedic, neurosurgical and maxillofacial procedures, although the dimensions and other characteristics vary depending on the application. In this case, threaded fasteners 64 are screwed directly into the bone. Washers 66 comprising shape memory material, having an outer diameter no greater than the diameter of heads 68 of the fasteners, are advantageous in enhancing the ease and security of closure, for the reasons explained above.

As another option, a shape memory washer of the type described above may be packaged inside a biodegradable material (plastic, such as polyglycolic acid, or a magnesium alloy), which holds the washer in its flattened form. In such embodiments, the washer will be released and begin to apply force against the head of fastener 64 only after the biodegradable material has been absorbed by the surrounding tissues (for example, 14-30 weeks after implantation). By this time, the fastener will have been biologically integrated with the bone.

Figure 5:
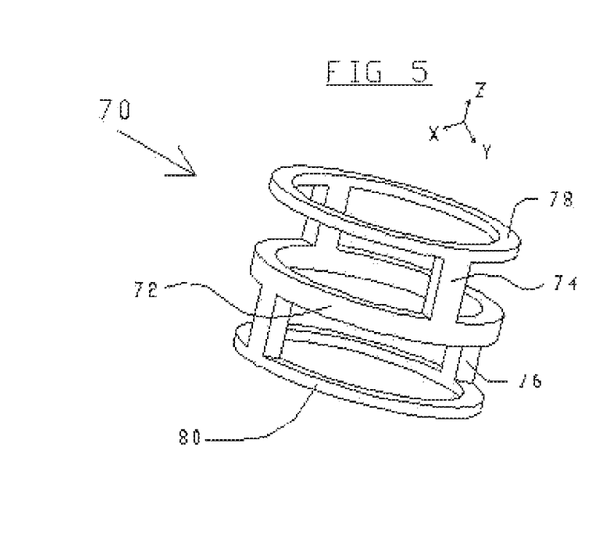
FIGS. 5 and 6 are schematic, pictorial views of a washer in relaxed and compressed states, respectively, in accordance with an embodiment of the present invention.
Figure 6:
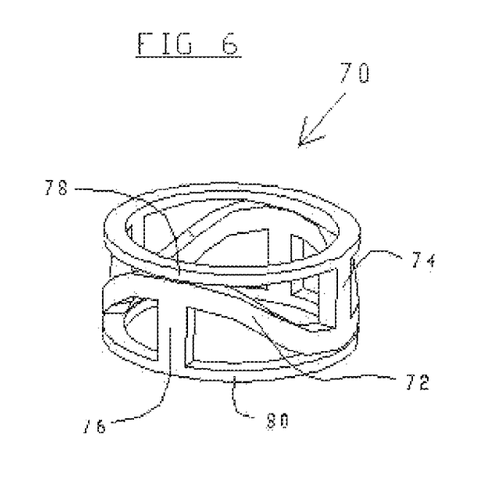

FIGS. 5 and 6 are schematic, pictorial views of a washer 70 in relaxed and compressed states, respectively, in accordance with an embodiment of the present invention. Washer 70 comprises a central ring 72, which is made from a shape memory material, such as Nitinol. The axis of the ring (and of the entire washer) is taken to be the Z-axis, as in the preceding embodiment. An annular ancillary structure, comprising struts 74, 76 and supporting rings 78, 80 is coupled to central ring 72. The struts and supporting rings may comprise the same material as the central ring, in which case the entire washer may be cut from a tube of Nitinol, using laser cutting techniques, for example. Alternatively, some or all of the elements of the ancillary structure may be made from other materials, such as titanium, and fastened to the central ring, by welding for example. In either case, heat treatment of the central ring is not required to give it the austenitic shape that is shown in FIG. 5.

The inner ends of axial struts 74 and 76 engage central ring 72 at different, respective circumferential locations on opposing sides of the central ring. The respective locations are offset from one another, with an offset of 90° in the present example. Although the struts shown in FIGS. 5 and 6 are relatively narrow and rectangular, other strut shapes and dimensions may alternatively be used. Further alternatively or additionally, a larger number of struts may be used. Each of the struts is connected at its outer end to one of supporting rings 78 or 80. Alternatively, other structural elements may be used to hold the outer ends of the struts in place between the head of the fastener and the underlying surface, so that rings 78 and 80 are not required.

Washer 70 fits around the shaft of a fastener, as illustrated, for example, in FIG. 1 or FIG. 4. As the fastener is tightened, the axial force exerted by the fastening element, such as the screw head, presses supporting rings 78 inward, toward one another, along the axis of the washer. Struts 74 and 76 therefore press inward, as well, and thus deform central ring 72 circumferentially into the wave shape shown in FIG. 6. At full compression of the washer, each strut presses the central ring into contact with the opposite supporting ring. The large tensile force generated in this position in the central ring is translated by the struts into an axial force against the head of the fastener. Washer 70 will generally resist shifting or deforming when there is a sharp impact on the fastener (such as when the patient bites down, in the dental application described above), so that the fastener is less likely to loosen.

As noted above, washer 70 absorbs energy as the fastener is tightened by tensioning a resilient, energy-absorbing component—in this case central ring 72. Nitinol, for example, reacts better to tension than to compression (elastic strain of 8% in tension, as opposed to about 5% in compression). Thus, the washer shown in FIGS. 5 and 6, as well as the washers shown in the figures that follow, is advantageous and unique in using tension (circumferential tension in the pictured embodiments) to store energy as the fastener is tightened and thereby prevent subsequent loosening of the fastener. This sort of fastening scheme, in which a ring in a washer is actually stretched as the washer is axially compressed, can be used not only with Nitinol and other shape memory materials, but also with other suitable types of elastic elements.

Figure 7:
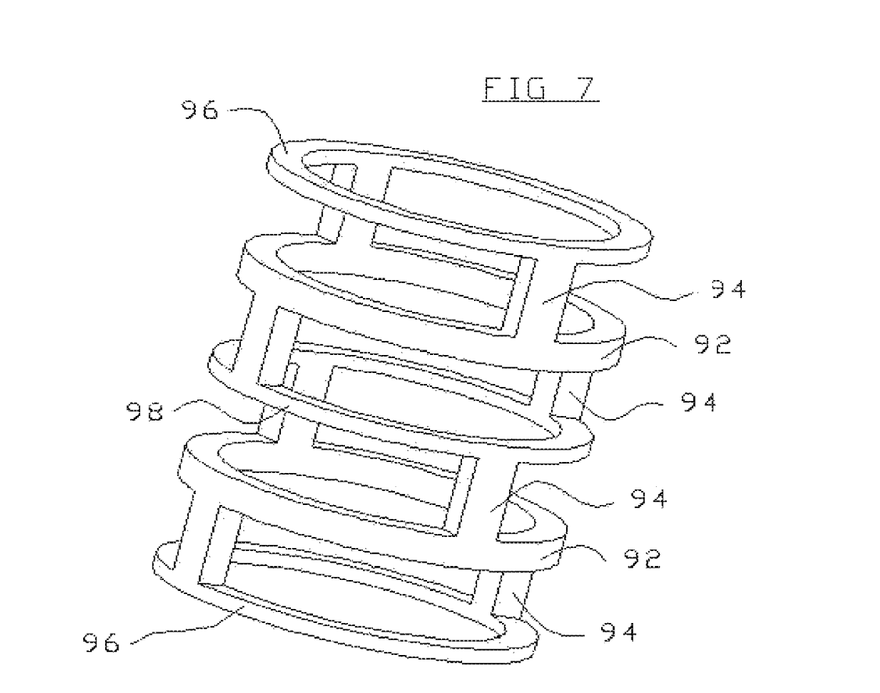
FIG. 7 is a schematic, pictorial view of a washer, in accordance with another embodiment of the present invention.

FIG. 7 is a schematic, pictorial view of a washer 90, in accordance with another embodiment of the present invention. This embodiment is similar in principle to washer 70 (FIGS. 5 and 6). Washer 90, however, comprises two or more central rings 92, made from shape memory material, spaced along the washer axis. The central rings are interconnected by multiple stages of axial struts 94 and supporting rings 96, 98. This configuration gives a larger range of axial compression than the preceding embodiment and exerts a stronger force against the head of the fastener. Alternatively or additionally, this larger range can enable washer 90 to absorb the same amount of energy as washer 70 while requiring less force to close the fastener. Optionally, supporting ring 98 may comprise shape memory material and thus serve as an additional central ring, giving a still larger range of compression and force.

Figures 8, 9:
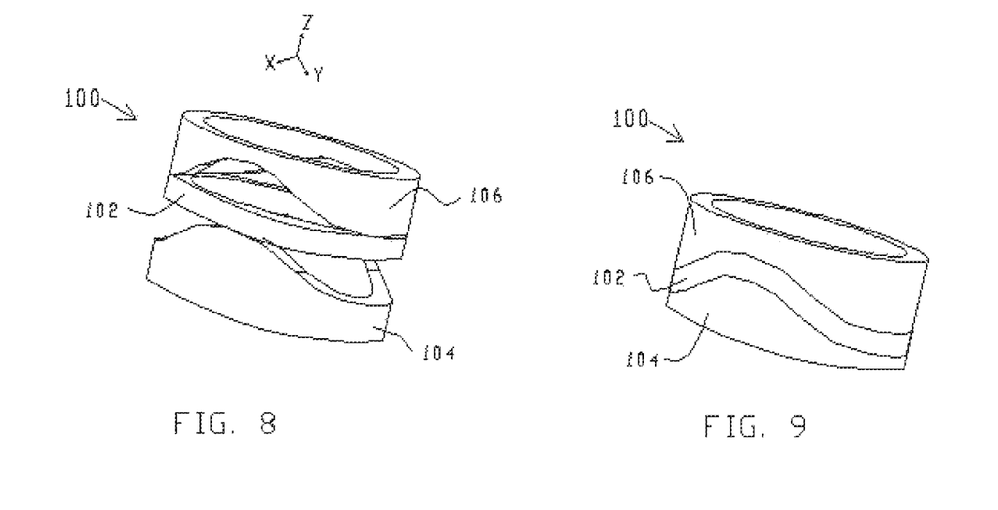
FIGS. 8 and 9 are schematic, pictorial views of a washer in relaxed and compressed states, respectively, in accordance with an alternative embodiment of the present invention.

FIGS. 8 and 9 are schematic, pictorial views of a washer 100 in relaxed and compressed states, respectively, in accordance with an alternative embodiment of the present invention. Here again, washer 100 comprises a central ring 102, made from a shape memory material, with an ancillary structure that causes the central ring to deform in response to axial force exerted on the washer. In this case, however, the ancillary structure comprises supporting rings 104 and 106, on opposing sides of the central ring along the Z-axis. Supporting rings 104 and 106 may also comprise shape memory material, or they may be made from other materials.

Supporting rings 104 and 106 have flat outer surfaces for engaging the head of the fastener and the underlying surface, while the inner surfaces of supporting rings 104 and 106, facing central ring 102, describe respective circumferential waves. These inner surfaces engage and deform the central ring in response to the axial force exerted on the outer surfaces. This deformation creates an outward axial force against the head of the fastener, as in the preceding embodiment.

The inner surfaces of rings 104 and 106 typically have interlocking profiles, as shown in the figures. As a result, when washer 100 is fully compressed, central ring 102 is supported on both sides by rings 104 and 106. Therefore, the central ring is prevented from shifting or deforming when there is a sharp impact on the fastener (such as when the patient bites down, in the dental application described above), so that the fastener is less likely to loosen.

Figure 10:
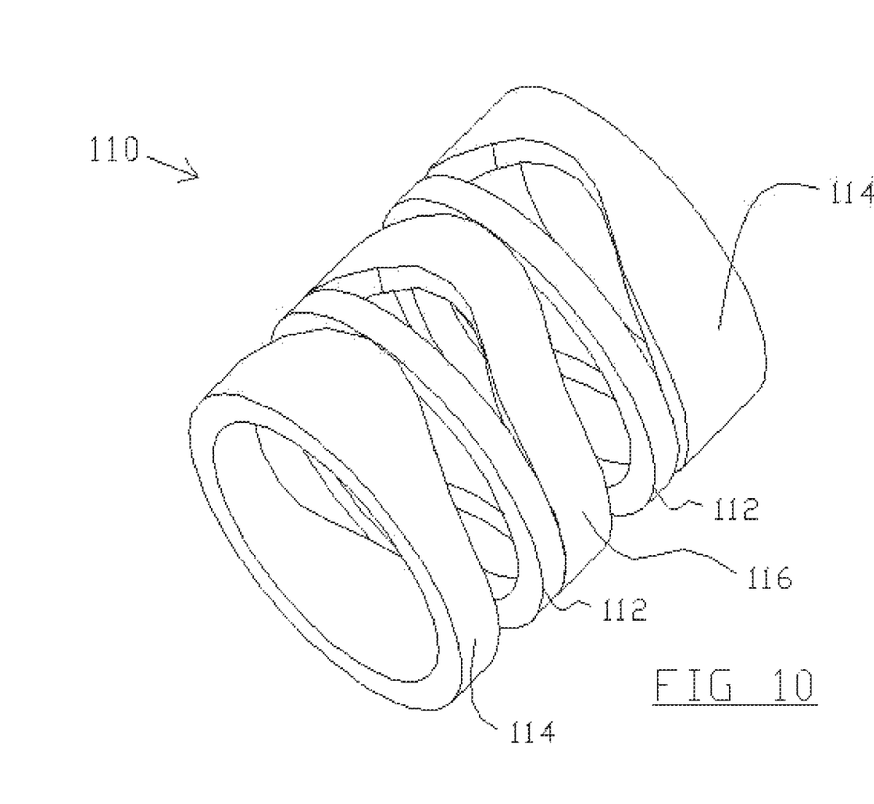
FIG. 10 is a schematic, pictorial view of a washer, in accordance with yet another embodiment of the present invention.

FIG. 10 is a schematic, pictorial view of a washer 110, in accordance with yet another embodiment of the present invention. This embodiment is similar in principle to washer 100 (FIGS. 8 and 9), but gives a larger range of axial compression and force (or greater energy storage with less force applied), like the embodiment of FIG. 7. Washer 110 comprises two or more central rings 112, made from shape memory material, spaced along the washer axis. The central rings are interconnected with multiple supporting rings 114, 116 having respective circumferential waves. Outer supporting rings 114 have the form of rings 104 and 106 described above, while inner supporting ring(s) 116 may have circumferential waves on both sides.

Figure 11:
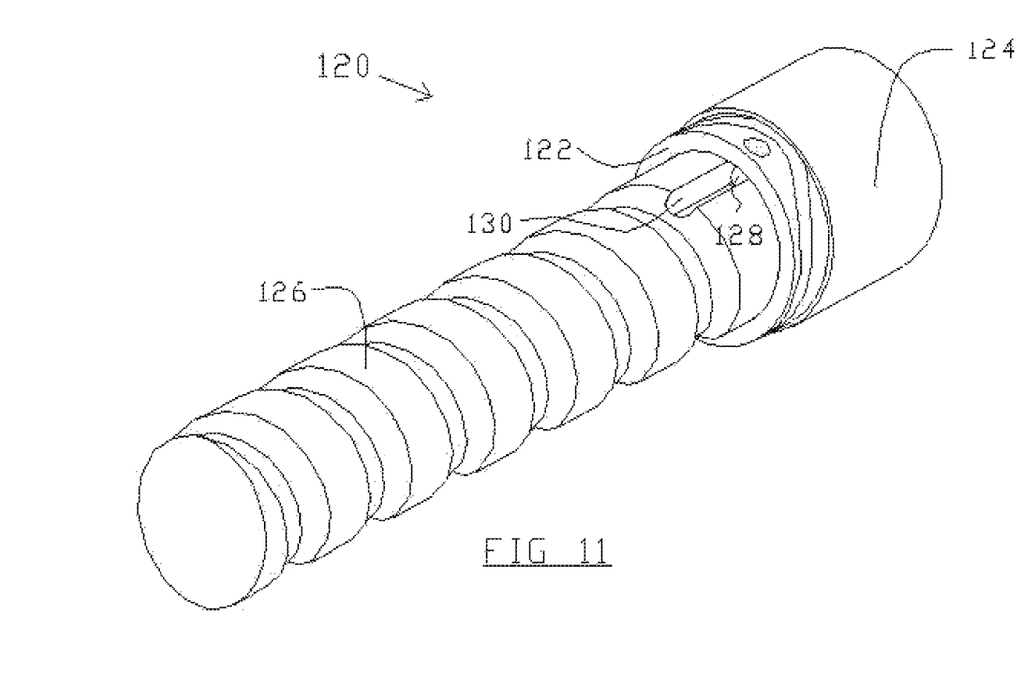
FIG. 11 is a schematic, pictorial view of a screw with an integral washer, in accordance with an embodiment of the present invention.

FIG. 11 is a schematic, pictorial view of a screw 120 with an integral washer 122, in accordance with an embodiment of the present invention. Washer 122 is similar in form to washer 100 (FIGS. 8 and 9), but is fixedly connected to screw 120. For this purpose, the washer may comprise a pin 128, which protrudes inward into a slot 130 in a shaft 126 of the screw. Alternatively, the washer may be attached to a head 124 of the screw, by laser welding, for example, or it may be fastened to the screw by other means or may be manufactured as a part of the screw itself. For instance, the head of the screw may have a curved lower surface, similar to the inner surfaces of rings 104 and 106, and thus obviate the need for a separate ring as part of the washer. Integration of the washer with the screw can make the assembly easier to handle and can also prevent relative rotation between the parts of washer as the screw is tightened, thereby facilitating optimal closure.

Although some of the embodiments described above relate specifically to medical (including dental) devices and procedures, the principles of the present invention may likewise be applied in other fields, and particularly precision applications, such as watch-making, micro-electronic tooling, eyeglasses, and fixation of optical components. It will thus be appreciated that the embodiments described above are cited by way of example, and that the present invention is not limited to what has been particularly shown and described hereinabove. Rather, the scope of the present invention includes both combinations and subcombinations of the various features described hereinabove, as well as variations and modifications thereof which would occur to persons skilled in the art upon reading the foregoing description and which are not disclosed in the prior art.

The invention claimed is:

1. Fastening apparatus, comprising:
    a fastener comprising a threaded shaft having a thread diameter and a fastening element having a head with a head diameter, greater than the thread diameter, such that a margin between the shaft and the head is less than 0.2 mm; and an annular washer, comprising a shape memory material, which is configured to fit over and surround the shaft so as to be compressed by the fastening element as the fastener is screwed into a socket and which has an outer diameter no greater than the head diameter.

2. The apparatus according to claim 1, wherein the shape memory material is formed so as to describe a circumferential wave in an austenitic state of the material.

3. The apparatus according to claim 1, wherein the shape memory material is formed as a ring, and wherein the annular washer comprises an ancillary structure configured to engender a circumferential deformation of the ring as the fastener is closed.

4. The apparatus according to claim 1, wherein the annular washer is fixedly connected to the fastener.

5. The apparatus according to claim 3, wherein the ancillary structure engenders a circumferential tension in the ring in response to the axial force.

6. The apparatus according to claim 3, wherein the central ring and the ancillary structure have a central opening configured to fit over and surround a threaded shaft of a fastener, having a head that exerts the axial force as the fastener is tightened into a socket.

7. The apparatus according to claim 3, wherein the ancillary structure comprises axial struts, which engage the central ring at different, respective circumferential locations on opposing sides of the ring.

8. The apparatus according to claim 7, wherein the struts have respective inner ends, which engage the central ring, and respective outer ends, opposite the respective inner ends, and wherein the ancillary structure comprises first and second supporting rings, each of which is connected to the outer ends of the struts on a respective one of the opposing sides of the ring.

9. The apparatus according to claim 8, wherein the struts connected to each of the supporting rings are configured to deform the central ring at the respective circumferential locations, in response to the axial force, so as to cause the central ring to contact the other of the supporting rings.

10. The apparatus according to claim 7, wherein the central ring is one of a plurality of central rings, which are disposed along the axis and are interconnected by the axial struts.

11. The apparatus according to claim 3, wherein the ancillary structure comprises first and second supporting rings, which are disposed along the axis on opposing sides of the central ring and have respective first and second inner surfaces describing respective first and second circumferential waves, which engage and deform the central ring in response to the axial force.

12. The apparatus according to claim 11, wherein the first and second supporting rings have flat outer surfaces, opposite the respective inner surfaces, for receiving the axial force, and wherein the first and second inner surfaces are configured so that the first and second circumferential waves interlock.

13. The apparatus according to claim 11, wherein the central ring is one of a plurality of central rings, which are disposed along the axis and are interconnected with multiple supporting rings with respective circumferential waves.

14. Apparatus for fixation, comprising:
    an implant, which is configured to be inserted into a bone and which comprises a threaded receptacle having a thread diameter;
    a fixture, which is configured to protrude outside the bone and comprises a socket for alignment with the threaded receptacle, the socket having a socket diameter greater than the thread diameter with a margin between the socket and the receptacle that is less than 0.2 mm;
    a fastener comprising a threaded shaft, which is configured to be screwed into the threaded receptacle, and a head, which is sized so as to fit closely inside the socket; and
    an annular washer, comprising a shape memory material, which is configured and sized to fit inside the socket while surrounding the shaft of the fastener so as to be compressed by the head as the fastener is screwed into the socket.

15. A fastening device, including an annular structure, which includes an elastic element and which is configured to fit over a threaded shaft of a fastener and to create a tension in the elastic element in response to an axial force exerted on the device by a head of the fastener as the fastener is tightened,
    wherein the head has a head diameter, such that a margin between the threaded shaft and the head is less than 0.2 mm, and wherein the elastic element has an outer diameter no greater than the head diameter.

16. The device according to claim 15, wherein the elastic element includes a shape memory material.

17. The device according to claim 16, wherein the shape memory material includes Nitinol.

\* \* \* \* \*

UNITED STATES PATENT AND TRADEMARK OFFICE
CERTIFICATE OF CORRECTION

| | | |
|---|---|---|
| PATENT NO. | : 8,834,539 B2 | Page 1 of 1 |
| APPLICATION NO. | : 13/127710 | |
| DATED | : September 16, 2014 | |
| INVENTOR(S) | : Dvir Keren et al. | |

It is certified that error appears in the above-identified patent and that said Letters Patent is hereby corrected as shown below:

On the title page, item (73), Assignee name should be NITILOCK LTD.

Signed and Sealed this
Twenty-third Day of December, 2014

Michelle K. Lee
*Deputy Director of the United States Patent and Trademark Office*